US006231659B1

(12) United States Patent
Hu et al.

(10) Patent No.: US 6,231,659 B1
(45) Date of Patent: May 15, 2001

(54) SIZING AGENTS AND STARTING MATERIALS FOR THEIR PREPARATION

(75) Inventors: Patrick C. Hu, Baton Rouge; Valerie N. LeGloahec, Lafayette; Michelle R. Free; Dixie E. Goins, both of Baton Rouge, all of LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/339,674

(22) Filed: Jun. 24, 1999

(51) Int. Cl.[7] .............................. C09D 7/00; D21F 11/00; C07D 307/36

(52) U.S. Cl. .................... 106/287.24; 106/211; 162/158; 162/168.1; 162/169; 162/175; 162/179; 549/255

(58) Field of Search ....................... 549/255; 106/287.24, 106/211; 162/158, 175, 179, 168.1, 169

(56) References Cited

U.S. PATENT DOCUMENTS

| | | | |
|---|---|---|---|
| 3,087,936 | 4/1963 | LeSuer | 260/326.3 |
| 3,102,064 | 8/1963 | Wurxburg et al. | 162/158 |
| 3,324,033 | 6/1967 | Knapp | 252/51.5 |
| 3,391,175 | 7/1968 | Davis | 260/448 |
| 3,391,219 | 7/1968 | Davis et al. | 260/683.15 |
| 3,476,774 | 11/1969 | Zaweski et al. | 260/346.8 |
| 3,623,985 | 11/1971 | Hendrickson | 252/51.5 A |
| 3,725,434 | 4/1973 | Elliott et al. | 260/326.3 |
| 3,726,822 | 4/1973 | von Bonin et al. | 260/29.6 RW |
| 3,821,069 | 6/1974 | Wurzburg | 162/158 |
| 3,855,251 | 12/1974 | Cahill | 260/346.8 R |
| 3,912,764 | 10/1975 | Palmer, Jr. | 260/346.8 |
| 3,927,041 | 12/1975 | Cengel et al. | 260/346.8 |
| 3,993,640 | 11/1976 | Pickard et al. | 536/30 |
| 4,086,251 | 4/1978 | Cengel et al. | 260/346.74 |
| 4,234,435 | 11/1980 | Meinhardt et al. | 252/51.5 A |
| 4,431,826 | 2/1984 | Sweeney | 549/255 |
| 4,576,680 | 3/1986 | Kawatani et al. | 162/158 |
| 4,839,415 | 6/1989 | Schurmann et al. | 524/549 |
| 4,883,886 | 11/1989 | Huang | 549/255 |
| 4,958,034 | 9/1990 | Hale et al. | 549/255 |
| 5,021,169 | 6/1991 | Shin et al. | 549/255 |
| 5,104,486 | 4/1992 | Sweeney | 162/158 |
| 5,114,538 | 5/1992 | Malatesta | 162/158 |
| 5,246,491 | 9/1993 | Takahashi et al. | 106/287.24 |
| 5,286,799 | 2/1994 | Harrison et al. | 525/285 |
| 5,319,030 | 6/1994 | Harrison et al. | 525/285 |
| 5,739,355 * | 4/1998 | Gateau et al. | 549/255 |
| 5,939,562 * | 8/1999 | Kapanen et al. | 549/255 |
| 6,001,166 * | 12/1999 | Ettl et al. | 106/287.2 |
| 6,015,776 | 1/2000 | Harrison et al. | 508/192 |
| 6,114,417 * | 9/2000 | O'Toole et al. | 524/27 |

FOREIGN PATENT DOCUMENTS

| | | |
|---|---|---|
| 0122617 | 10/1984 | (EP) . |
| 0169250 | 1/1986 | (EP) . |
| 1422302 | 1/1976 | (GB) . |
| 1588416 | 4/1981 | (GB) . |
| 2082067 | 3/1982 | (GB) . |
| 9611193 | 4/1996 | (WO) . |

OTHER PUBLICATIONS

CAPLUS Abstract of JP 57154495 dated 1982.

WPIDS Abstract of JP 57154495 dated 1982.

Fleckner, et al., "Tricarbonylbis(n2–cis–cyclooctene)iron: Photochemical Synthesis of a Versatile Fe(CO)3 Source for Olefin Isomerization and Preparative Applications", J. Am. Chem. Soc., 1984, vol. 106, pp. 2027–2032.

Kane, et al., "Catalytic Isomerisation of Alkenes by Fe(CO)4", Polyhedron, vol. 4, No.4, 1985, pp. 533–538.

Darsillo, et al., "Photoassisted Catalysis of the 1–Pentene Isomerization by Fe(CO)5 Physisorbed onto Porous Vycor Glass", Inorg. Chem., 1988, vol. 27, pp. 2815–2819.

XP–002144388 –Derwent Abstract of JP 05 039390, issued 1993.

XP–002144389 –Derwent Abstract of JP 54 028389, issued 1979.

CAPLUS Abstract of JP 57154495 dated 1982.

WPIDS Abstract of JP 57154495 dated 1982.

Kirk–Othmer, Encyclopedia of Chemical Technology, 3rd Edition, vol. 16, John Wiley & Sons, 1981, pp. 803–825.

Encyclopedia of Polymer Science and Technology, Plastics, Resins, Rubbers, Fibers, vol. 9, John Wiley & Sons, Inc., 1968, pp. 748–793.

* cited by examiner

*Primary Examiner*—Deborah C. Lambkin
(74) *Attorney, Agent, or Firm*—Phillip M. Pippenger

(57) ABSTRACT

The sizing agents are mixtures of alkenyl succinic anhydrides in which the alkenyl groups have in the range of about 6 to about 40 carbon atoms, and in which at least 97 wt % of the alkenyl groups are bifurcated on the alpha carbon atom into two branches neither of which has less than two carbon atoms. Other characteristics of the mixture are that (1) 20–50% of the bifurcated alkenyl groups have only one methyl or methylene substituent and no other side chain, and the remainder of such bifurcated groups have two straight chain branches (no side chain) emanating from the alpha carbon atom, (2) at least 3 alkenyl succinic anhydrides that differ in the number of alkenyl carbon atoms are each present in at least 5 wt % in the mixture, (3) no more than about 50 wt % of the alkenyl succinic anhydrides is any given alkenyl succinic anhydride or mixture of isomers having the same number of carbon atoms in their alkenyl groups, (4) the average number of carbon atoms in the alkenyl groups is ca. 16–22 per molecule, and (5) the mixture has a viscosity at 25° C. in the range of about 80 to about 220 centistokes.

19 Claims, No Drawings

SIZING AGENTS AND STARTING MATERIALS FOR THEIR PREPARATION

BACKGROUND

Heretofore, certain alkenyl succinic anhydrides have been developed for use as paper sizing agents. If the ultimate treated paper is for indirect food usage, regulations in the United States require that 95 wt % of the olefins used in forming the alkenyl succinic anhydride must be in the $C_{16}$ to $C_{20}$ range. One typical commercial product sold for such use is an alkenyl succinic anhydride in which the alkenyl group is derived from a mixture of internal olefins composed on a weight basis of approximately 4% $C_{14}$, 50% $C_{16}$, 45.5% $C_{18}$, and 0.5% $C_{20}$ olefins. This olefin mixture is also used as a component of certain drilling fluids. Another commercially used mixture of alkenyl succinic anhydrides is formed from an internal olefin mixture consisting essentially of $C_{16}$ and $C_{18}$ olefins.

Various other alkenyl succinic anhydrides have been proposed for use as paper sizing agents. See, for example, U.S. Pat. Nos. 3,102,064; 3,821,069; 4,431,826; 4,576,680; 5,114,538; and 5,246,491; EP published application 0 169 250 A1; and Japan Kokai 57-154495.

Commercial processes for producing olefins typically produce a range of olefins of differing molecular weights. Use of distillation enables the resultant gross mixtures of olefins to be divided into various carbon number fractions to thereby provide olefins for specified end use applications. Typically $C_6$ and $C_8$ olefins find commercial application as comonomers in the manufacture of olefin polymers. $C_8$ and $C_{10}$ olefins are used in the production of synthetic lubricants, while $C_{12}$ olefins are very useful in the manufacture of synthetic household detergents and surface active agents. And as noted above, olefin mixtures highly enriched in $C_{16}$ and $C_{18}$ olefins are of commercial utility as raw materials for the synthesis of paper sizing agents and as components of drilling fluids.

It would be of considerable benefit if new, useful olefin mixtures could be developed that would make possible more efficient utilization of olefins for which relatively small utilities currently exist. If this could be accomplished, current market demands for olefins could continue to be efficiently served by present and projected manufacturing facilities while at the same time making more efficient use of hydrocarbon feedstocks to such facilities and product outputs from such facilities.

This invention is deemed to make possible the fulfillment of the foregoing objective.

SUMMARY OF THE INVENTION

Pursuant to this invention there are provided both new sizing agents and new olefin mixtures useful in producing such sizing agents. More particularly, one embodiment of this invention makes it possible to provide new sizing agents with properties rendering them useful in the manufacture of a variety of products, such as paper, cardboard, wall board, gypsum board, and like materials. In another of its embodiments this invention provides new olefin mixtures which are especially adapted for use as raw materials for the manufacture of such sizing agents. Moreover, other potential applications exist for various new compositions of this invention.

Thus, in accordance with one of its embodiments this invention provides a mixture of alkenyl succinic anhydrides in which the alkenyl groups have in the range of about 6 to about 40 carbon atoms, and in which at least 97 wt % (preferably at least 98 wt %) of the alkenyl groups are bifurcated on the alpha carbon atom into two branches neither of which has less than two carbon atoms, said mixture being further characterized in that:

A) from about 20 to about 50% of the alkenyl succinic anhydrides that are bifurcated on the alpha carbon atom, have only one methyl or methylene group thereon, and the remainder of the alkenyl succinic anhydrides that are bifurcated on the alpha carbon atom have two straight chain branches emanating from the alpha carbon atom;

B) the alkenyl succinic anhydrides present in the mixture are composed of at least 3 (and preferably at least 4) alkenyl succinic anhydrides that differ from each other in the number of carbon atoms in the respective alkenyl groups, each of these at least 3 (or preferably at least 4) alkenyl succinic anhydrides being present in said mixture in an amount of at least 5 wt % based on the total weight of said mixture of alkenyl succinic anhydrides;

C) the alkenyl succinic anhydrides present in the mixture contain no more than about 50 wt % (preferably no more than about 40 wt %) based on the total weight of the alkenyl succinic anhydrides, of any specific alkenyl succinic anhydride;

D) the alkenyl succinic anhydrides present in the mixture contain no more than about 50 wt % (preferably no more than about 40 wt %) based on the total weight of the alkenyl succinic anhydrides, of any two or more alkenyl succinic anhydride isomers having the same number of carbon atoms in their alkenyl groups;

E) the alkenyl succinic anhydrides present in the mixture are proportioned such that the average number of carbon atoms in the alkenyl groups thereof is in the range of about 16 to about 22 (preferably in the range of about 16 to about 20) carbon atoms per molecule; and F) the mixture of alkenyl succinic anhydrides has a viscosity at 25° C. in the range of about 80 to about 220 centistokes.

Such mixtures can be formed by reaction of the appropriate mixture of olefins with maleic anhydride at a suitable temperature at which the so-called "ene" reaction occurs (e.g., 250° C.). The mixture of olefins used to make the alkenyl succinic anhydrides (and thus the alkenyl groups of the mixture of alkenyl succinic anhydrides produced) can have odd numbers of carbon atoms or even numbers of carbon atoms, or can be mixtures of odd and even numbered olefins and alkenyl groups. Alkenyl succinic anhydrides produced from olefin mixtures in which all olefin components, or substantially all olefin components (e.g., at least about 95 wt % of the olefins) are even numbered olefins, are preferred.

Alternatively, the alkenyl succinic anhydrides mixtures of this invention can be prepared by blending together in appropriate proportions two or more preformed alkenyl succinic anhydrides in which the alkenyl groups differ from each other such that the resultant blend conforms to the requirements of the mixtures of this invention.

Mixtures of alkenyl succinic anhydrides as described above wherein the components thereof have in the range of about 12 to about 30 carbon atoms in their respective alkenyl groups are preferred. More preferred are mixtures of alkenyl succinic anhydrides as described above wherein the components thereof have in the range of about 14 to about 26 carbon atoms. Mixtures of alkenyl succinic anhydrides as described above wherein the mixture contains, if any, no more than a total of about 50 wt % (and even more preferably no more than about 10 wt %) of alkenyl succinic anhydrides in which the alkenyl groups contain 16, 17 or 18 carbon atoms are particularly preferred from the cost-effectiveness standpoint. In fact, it has been found possible to effectively utilize mixtures of alkenyl succinic anhydrides which are essentially devoid of alkenyl groups containing 15, 16, 17, 18, or 19 carbon atoms, i.e., such mixtures contain, if any, no more than trace amounts, say 2% at most, of alkenyl groups containing 15 to 19 carbon atoms.

Preferably, the mixtures of alkenyl succinic anhydrides of this invention are further characterized in that at least about 70 wt % of the alkenyl groups have the olefinic double bond in the two or higher position.

The various mixtures described above can be in admixture with relatively small amounts of one or more saturated aliphatic hydrocarbons. The amount of such saturated aliphatic hydrocarbon content, when present, will typically be up to about 5 wt % (more usually up to about 2 wt %) based on the total weight of the alkenyl succinic anhydrides and the saturated aliphatic hydrocarbon(s) present in the composition.

Particularly preferred is a mixture of alkenyl succinic anhydrides as described above wherein (1) from about 20 to about 80 wt % of the alkenyl succinic anhydrides in the mixture have $C_{14}$ alkenyl groups, and (2) from about 20 to about 80 wt % of the alkenyl succinic anhydrides present in the mixture have alkenyl groups having in the range of 20 to 26 carbon atoms, the total of the percentages of (1) and (2) being at least 90 wt %, and more preferably at least 98 wt %, and especially mixtures of this type wherein the alkenyl groups that are in the range of $C_{20}$ to $C_{26}$ have even numbers of carbon atoms.

The alkenyl succinic anhydrides of this invention can be hydrogenated to produce the corresponding alkyl succinic anhydrides. Accordingly, this invention also provides a mixture of alkyl succinic anhydrides corresponding to each and every mixture of alkenyl succinic anhydrides disclosed in any portion of this document, including the claims hereof.

Other embodiments of this invention relate to new mixtures of internal olefins from which alkenyl succinic anhydrides of this invention can be prepared. One such embodiment is a hydrocarbon mixture in which the components thereof have in the range of about 6 to about 40 carbon atoms in the molecule, and in which at least 97 wt % (and preferably at least 98 wt %) of the internal olefins have the olefinic double bond in the two or higher position, said hydrocarbon mixture being further characterized in that:

A) said hydrocarbon mixture is composed of a plurality of aliphatic olefins, optionally in admixture with (i) at least one saturated hydrocarbon, (ii) at least one aromatic hydrocarbon free of unsaturation other than aromatic unsaturation, or (iii) a combination of (i) and (ii), the total amount of (i) and (ii) being up to about 15 wt % based on the total weight of said hydrocarbon mixture;

B) from about 20 to about 50% of the internal olefins have only one methyl group thereon and the remainder of the internal olefins are devoid of any branching;

C) the internal aliphatic monoolefins present in the hydrocarbon mixture are composed of at least 5 wt % based on the total weight of the internal aliphatic monoolefins, of each of at least 3 (preferably at least 4) internal aliphatic monoolefins that differ from each other in the number of carbon atoms in the molecule;

D) the internal aliphatic monoolefins present in the hydrocarbon mixture contain no more than about 50 wt % (preferably no more than about 40 wt %) based on the total weight of the internal aliphatic monoolefins, of any one specific internal aliphatic monolefin;

E) the internal aliphatic monoolefins present in the hydrocarbon mixture contain no more than about 50 wt % (preferably no more than about 40 wt %) based on the total weight of the internal aliphatic monoolefins, of any two or more internal aliphatic monolefin isomers having the same number of carbon atoms;

F) the internal aliphatic monoolefins present in the mixture are proportioned such that the average number of carbon atoms in the mixture is in the range of about 16 to about 22 carbon atoms, and preferably in the range of about 16 to about 20 carbon atoms; and G) the mixture of internal aliphatic monoolefins, if reacted at 250° C. with maleic anhydride in proportions of 2 moles of such olefins per mole of maleic anhydride in an uncatalyzed ene reaction, can produce an alkenyl succinic anhydride having a viscosity at 25° C. in the range of about 80 to about 220 centistokes.

More preferred are hydrocarbon mixtures as described above wherein the components thereof have in the range of about 12 to about 30 carbon atoms in the molecule. Still more preferred are hydrocarbon mixtures as described above wherein the components thereof have in the range of about 14 to about 26 carbon atoms in the molecule.

Still another embodiment is a hydrocarbon mixture as described above wherein:

A) the components of the hydrocarbon mixture have in the range of about 12 to about 30 carbon atoms (and preferably in the range of about 14 to about 26 carbon atoms) in the as molecule;

B) the hydrocarbon mixture (a) is composed of a plurality of aliphatic olefins in admixture with one or more saturated aliphatic hydrocarbons, the amount, if any, of such one or more saturated aliphatic hydrocarbons being up to about 5 wt % (preferably up to about 2 wt %) based on the total weight of the hydrocarbon mixture, and (b) is devoid of any aromatic hydrocarbon; and C) at least 98 wt % of the internal aliphatic monoolefins present in the hydrocarbon mixture have an odd number of carbon atoms, and even more preferably, an even number of carbon atoms in their respective molecules.

Optionally, but preferably, the hydrocarbon mixtures of this invention contain, if any, no more than about 10 wt % (and more preferably no more than about 2 wt %) of olefins having in the range of 16 to 18 carbon atoms in the molecule.

Yet another embodiment is a hydrocarbon mixture consisting essentially of (i) at least one $C_{14}$ aliphatic internal monoolefin, (ii) at least one $C_{18}$ aliphatic internal monoolefin, (iii) at least one $C_{20}$ aliphatic internal monoolefin, (iv) at least one $C_{22}$ aliphatic internal monoolefin, (v) at least one $C_{24}$ aliphatic internal monoolefin, at least 97 wt % (and preferably at least 98 wt %) of the internal monoolefins of this mixture having the olefinic double bond in the two or higher position, said mixture optionally additionally containing (vi) one or more saturated aliphatic hydrocarbons having in the range of about 18 to about 24 carbon atoms in the molecules in an amount of up to about 5 wt % based on the total weight of the mixture, this mixture containing from about 20 to about 80 parts by weight of (i) per each part by weight of the combination of (ii), (iii), (iv), and (v).

A further embodiment of this invention is a process of sizing a cellulose fiber in an aqueous paper-making slurry, the process being improved by introducing into the slurry as a sizing agent an alkenyl succinic anhydride mixture of this invention. In the practice of this embodiment, the use of preferred mixtures of alkenyl succinic anhydrides is itself preferred. A feature of this embodiment is that the alkenyl succinic anhydride mixtures of this invention can be used as the sole internal sizing agent or the alkenyl succinic anhydride mixtures of this invention can be used in combination with other known internal paper sizing agents such as alkenyl ketene dimer and/or conventional alkenyl succinic anhydride sizing agents. The sizing process itself can be conducted in any known manner and the details of the process form no part of this invention. The important feature provided by this invention is the use in a conventional manner of a novel and eminently useful alkenyl succinic anhydride mixture which greatly enhances the overall sizing operation.

Other embodiments and features of this invention will become still further apparent from the ensuing description and the appended claims.

FURTHER DETAILED DESCRIPTION

Olefin Mixtures

The olefin mixtures of this invention are composed of two kinds of olefrns, viz., (1) one or more straight chain internal olefins having no branching whatever, and (2) one or more internal olefins that have one and only one methyl group as a side chain, the rest of the molecule being a straight chain internal olefin. And as noted above, the mixture must meet all of the other requirements described above.

In addition to the characteristics described above, there are a few additional points worthy of note concerning the olefins. First of all, the olefin mixtures of this invention are formed by blending together the requisite number and amounts of the olefins to form the desired blend of this invention. Thus at least two separate olefin feedstocks are used, at least one of which must itself be a mixture or cut of olefins that will produce a blend that meets the requirements of the olefin mixtures of this invention. For example, if a substantially pure $C_{14}$ olefin is one of the feedstocks to the blending vessel and only two feedstocks are to be used, the other feedstock must comprise at least three olefins of different carbon contents such that the finished blend will contain at least four olefins of different carbon numbers per molecule. Moreover, the identities and amounts of the olefins being blended must be such as to provide a finished blend that meets all of the other requirements of the olefin mixtures of this invention as described above. There is, of course, no limitation on the number of olefin feedstocks that are employed in the blending operation provided that the finished mixture contains at least 5 wt % of at least 4 olefins of different carbon contents, and the other requirements of this invention are met by the finished blend.

The blending can be conducted at room temperature when the components and the proportions thereof are such that the resultant blend is a liquid at room temperature. Alternatively, the blending can be conducted at suitable elevated temperatures in order to facilitate the blending where solid olefin components are being fed into the blending vessel.

Typically all of the individual olefin components of the mixture are predominately, if not exclusively, internal olefins. However depending upon the source and processing used in their manufacture, there may be a small content of 1-olefins in the mixture. As long as the content of 1-olefins, if any, in the finished olefin mixture does not exceed about 2 wt %, and preferably is no more than 1 wt %, the presence of such 1-olefins is included within the scope of this invention.

Preferably, the internal double bond of the internal olefins is in at least the 3-position, and thus in preferred olefin mixtures of this invention at least 70 wt % of the internal olefins have the olefinic double bond in the 3 or higher position.

Another characteristic of the olefins used is that they are made up of linear or substantially linear internal olefins or they are made up of linear or substantially linear olefins in admixture with vinylidene olefins. If the mixtures are mixtures of substantially linear olefins, the mixture will normally contain at least 95 wt % of linear olefins. If the mixtures are mixtures of substantially linear olefins and vinylidene olefins, the mixtures will typically contain in the range of about 50 to about 90 wt % of linear olefins, and in the range of about 10 to about 50 wt % of vinylidene olefins. Typically the preferred $C_{14}$ olefins used in the olefin mixtures of this invention will contain no more than about 15 wt % of vinylidene or other branched olefins, if any. On the other hand, the $C_{20}$ to $C_{26}$ olefins used in the preferred olefin mixtures of this invention will contain in the range of about 50 to 65 wt % of linear olefins with the balance to 100 wt % being essentially entirely vinylidene olefins.

For best results the internal olefins used in the practice of this invention will be formed by isomerizing alpha-olefins formed by alkyl aluminum chain growth of ethylene. For details of such chain growth technology, see for example, U.S. Pat. Nos. 3,391,175 and 3,391,219. The olefin components of the product mixtures formed by ethylene chain growth are predominately alpha-olefins. Process technology for isomerizing alpha-olefins to internal olefins is also well known and reported in the literature. See, for example, Fleckner et al., *J. Am. Chem. Soc.,* 1984, 106, 2027–2032; Kane et al., *Polyhedron,* 1985, 4, 533–538; and Darsillo et al., *Inorg. Chem.,* 1988, 27, 2815–2819 which describe catalytic photoinitiated isomerization of alpha-olefins to internal olefins using iron pentacarbonyl as the catalyst.

Other hydrocarbons such as saturated hydrocarbons, aromatic hydrocarbons, and dienes, can be present in small amounts in the olefin mixtures of this invention. Such components can result from the processing used in the production of one or more of the olefins used in forming the finished olefin mixture. Of these impurities, paraffinic hydrocarbons are of least concern and in some cases can prove useful as fluidization agents for processes in which the olefin mixture is employed. Thus amounts of saturated aliphatic hydrocarbons of up to about 20 wt % can be present in the olefin mixtures of this invention. Aromatic hydrocarbons are also acceptable as long as they are free of unsaturated side chains. Amounts thereof of up to about 10 wt % are acceptable in the olefin blends of this invention. If a mixture of saturated aliphatic and aromatic hydrocarbons is present, the total amount is preferably not greater than about 25 wt % based on the total weight of the overall mixture of hydrocarbons including the olefin mixture. Dienes and other reactive unsaturated impurities, if present, should be kept below about 10 wt % in the olefin mixtures of this invention.

Alkenyl Succinic Anhydride Mixtures

The essential requirements and characteristics of these mixtures have been described above. It is important to observe, however, that the alkenyl succinic anhydrides mixtures of this invention are formed from synthetic olefins, and not from polymers such as polyethylene, polypropylene, polybutylene, or polyisobutylene.

The alkenyl groups of substantially all (e.g., at least 95%) of the alkenyl succinic anhydrides in the mixtures of this invention typically are bifurcated on the alpha carbon atom into two branches, one of which contains an olefinic double bond and the other of which is saturated. Preferably, neither of such branches contains less than two carbon atoms.

Methods for preparing alkenyl succinic anhydrides from olefins and maleic anhydride are well known and are reported in the literature. Preferably the process used will be a thermal process wherein the ene reaction takes place. If desired, one or more additives can be included in the reaction mixture to inhibit color tar, or polymer formation during the thermal process. See, for example, U.S. Pat. Nos. 4,958,034 and 5,021,169 and references cited therein, for details concerning the thermal process and use of additives therein to inhibit tar and color formation. The use of such additives may not be required, however, especially if the process is performed at a temperature in the range of about 240 to about 250° C. using an excess of olefin, and the reaction is terminated before reaching complete conversion.

As noted above, there are basically two different ways by which the alkenyl succinic anhydride compositions of this invention can be prepared. One method comprises producing at least two different alkenyl succinic anhydrides and then blending these products together in suitable proportions in order to produce a mixture meeting the requirements of the alkenyl succinic anhydride mixtures of this invention. For example, a substantially pure tetradecenyl succinic anhydride can be prepared by reacting a $C_{14}$ internal olefin with maleic anhydride in an uncatalyzed ene reaction. In another preparation maleic anhydride can be reacted with a mixture of $C_{20}$ to $C_{26}$ even-numbered olefins in a similar ene reaction to form a corresponding mixture of alkenyl succinic anhydrides. By blending together these two respective alkenyl succinic anhydride compositions, it is possible to produce mixtures meeting the requirements of the alkenyl succinic anhydride mixtures of this invention. Thus if desired, at least three individual pure alkenyl succinic anhydrides having different alkenyl groups collectively meeting the requirements of this invention, can be individually prepared and then blended together in appropriate proportions to form alkenyl succinic anhydride mixtures of this invention.

The other basic method for producing the alkenyl succinic anhydride mixtures of this invention is the preferred general method for use. This method involves preparing an appropriate mixture of the requisite olefins meeting the requirements of this invention, and subjecting this mixture to an uncatalyzed ene reaction with maleic anhydride to produce the alkenyl succinic anhydride mixture of this invention in a single ene synthesis reaction.

Methods for using alkenyl succinic anhydrides for sizing paper and related products is also well known. See, for example, U.S. Pat. No. 5,114,538 and references cited therein. Thus, in conducting the sizing operation in the manufacture of paper a conventional filler such as, for example, precipitated calcium carbonate, will typically be used in combination with the sizing agent of this invention. Ordinarily a sizing amount of an alkenyl succinic anhydride mixture of this invention is used, and this amount typically falls in the range of from about 0.005 to 2% by weight based on the weight of the dried fibers or dried pulp.

By virtue of the broader range of alkenyl groups in the alkenyl succinic anhydride mixtures of this invention as compared to conventionally-used $C_{16}$–$C_{18}$ alkenyl succinic anhydride sizing agents, improved sizing efficacy may be achieved while at the same time achieving good emulsification in the aqueous media used.

Alkyl Succinic Anhydride Mixtures

Hydrogenation of the alkenyl succinic anhydrides of this invention results in the production of corresponding mixtures of alkyl succinic anhydrides of this invention. The hydrogenation is typically performed under a pressurized hydrogen atmosphere using a suitable catalyst such as platinum on charcoal. Such procedures are known and reported in the literature.

Illustrative Examples

The efficacy of this invention was demonstrated in a series of experiments in which various olefin compositions of this invention were prepared, alkenyl succinic anhydride mixtures of this invention were formed from these olefin compositions, and tests were performed using the alkenyl succinic anhydride mixtures. Examples 1–6 describe the preparation of six alkenyl succinic anhydride mixtures of this invention, and identify the olefin mixtures of this invention used in forming these anhydride mixtures.

EXAMPLE 1

A commercially available mixture of $C_{18-30}$ alpha olefins from British Petroleum/Amoco Corporation was obtained for use in preparing an alkenyl succinic anhydride of this invention. This mixture was filtered through a short pad of activated alumina in a chromatographic column to remove traces of polar compounds present in the mixture. $^{1}$H NMR analysis of the so-treated olefin mixture indicated that it contained on a normalized mole percentage basis 31.3% of vinyl olefins, 10.5% of internal olefins, 56.8% of vinylidene olefins, and 1.4% of trisubstituted olefins. In addition only 0.066 wt % of ether impurity was present. Ester and alcohol impurities, if any, were below detection level.

Table 1 sets forth the molecular weight distribution of this mixture of alpha olefins in terms of GC area percentages:

TABLE 1

| Olefin Carbon Number | GC Area Percent |
|---|---|
| Below $C_{18}$ | 0.05 |
| $C_{18}$ | 1.30 |
| $C_{20}$ | 57.24 |
| $C_{22}$ | 30.68 |
| $C_{24}$ | 8.96 |
| $C_{26}$ | 1.33 |
| $C_{28}$ | 0.20 |
| $C_{30}$ | 0.04 |
| $C_{32}$ | nil |

A nitrogen-dried 5-liter Büchi stainless steel reactor, equipped with a mechanical stirrer, a thermocouple well, and a nitrogen inlet tube, was charged with the purified $C_{18-30}$ alpha olefin mixture (2520 grams) and iron pentacarbonyl (1.4–1.5 mL) with the aid of a cannula. The mixture was heated with a circulating oil bath on the reactor jacket at 200° C. while stirring the olefin mixture for a period of 4.5 hours. During this time, a pressure build-up of approximately 5 psi occurred. At the end of the reaction, the hot liquid isomerization mixture was cooled to 150° C. The reactor was then discharged under a nitrogen atmosphere. The resultant internal $C_{18-30}$ olefin mixture was purified by distillation under reduced pressure. Its boiling range was 170–190° C. at approximately 1 torr.

EXAMPLE 2

A mixture of alkenyl succinic anhydrides was produced using the isomerized olefin mixture formed in Example 1. This synthesis was conducted in a nitrogen-dried 1-liter Parr stainless steel reactor, equipped with a mechanical stirrer, a thermocouple well, and a nitrogen inlet tube. Into the reactor were charged maleic anhydride (77 grams, 1 equivalent) and $C_{18-30}$ isomerized olefin mixture (451 grams, 2 equivalents). The vessel was then bolted to the reactor frame, and the reaction mixture was purged with nitrogen for 15 minutes. The mixture was stirred with a double helical impeller at 900 rpm and heated with an electrical mantle on the reactor jacket. The mixture reached 180° C. at a pressure of 45 psi in 30 minutes. After 3 hours at 230° C., the hot amber liquid was quickly discharged through the bottom valve of the reactor into a 2-liter Erlenmeyer flask under a nitrogen atmosphere. Unreacted olefin and maleic anhydride were stripped from the reaction mixture using a 4-liter Kuigelrohr apparatus up to a final pot temperature of 150° C. at 0.5 torr.

EXAMPLE 3

In order to prepare another alkenyl succinic anhydride for use in forming an alkenyl succinic anhydride mixture of this invention, use was made as the olefinic starting material of a $C_{14}$ internal olefin from Chevron Chemical Company. This olefin when subjected to $^1H$ NMR analysis was found to contain on a normalized mole percentage basis 1.5% of vinyl olefin, 84.7% of internal olefin, 12.7% of trisubstituted olefin, and 1.1% of vinylidene olefin. Of the internal olefin content, 17.2% was indicated to be the 2-tetradecene, and 67.5% was indicated to have the double bond in the 3 or higher position.

The procedure of Example 2 was utilized in carrying out the ene reaction to produce the alkenyl succinic anhydride except that the reactants were used in the following amounts: 304 grams (1.55 equivalents) of the internal olefin and 99 grams of maleic anhydride. In addition the reaction was performed in a Parr reactor instead of a Büchi reactor. In the present reaction the mixture reached 225° C. at a pressure of 60 psi in 40 minutes. After 2.5 hours at 230° C., the hot amber liquid was quickly discharged through the bottom valve of the reactor into a 2-liter Erlenmeyer flask under a nitrogen atmosphere. The unreacted olefin and maleic anhydride were stripped from the reaction mixture in the 4-liter Kügelrohr apparatus to a final pot temperature of 110° C. at 0.5 torr. The resultant alkenyl succinic anhydride product was then distilled under reduced pressure (200–220° C. at about 1 torr) to yield a white pasty solid.

EXAMPLE 4

Six different alkenyl succinic anhydride mixtures of this invention were prepared by blending together measured quantities of the alkenyl succinic anhydrides produced in Examples 2 and 3. The blends were prepared by mixing in a reaction vessel the quantities of the respective alkenyl succinic anhydrides set forth in Table 2.

TABLE 2

| Wt. Ratio of $C_{14}/C_{18-30}$ Alkenyl Succinic Anhydrides | Average Carbon Number in the Alkenyl Groups of the Mixture |
|---|---|
| 70/30 | 16.1 |
| 60/40 | 16.8 |
| 50/50 | 17.5 |
| 40/60 | 18.2 |
| 30/70 | 18.9 |
| 20/80 | 19.6 |

EXAMPLE 5

The viscosities of the alkenyl succinic anhydride compositions of this invention (ASA) formed in Example 4 were determined at 25° C. using a Brookfield Digital Viscometer, Model LVDVII Plus operated at a shear rate of 15.8 reciprocal seconds. The procedure used is as follows:

1) The small sample adapter is inserted into its housing, and temperature control is established by circulating constant temperature fluid through the housing.
2) The viscometer alignment is checked, and adjusted if necessary. The viscometer is switched on and an automatic strain gauge zeroing is performed.
3) The test sample is added to the small sample adapter.
4) An appropriate spindle and rotation velocity combination is selected so that the strain gauge reading falls between 20% and 100% of full scale. Once the spindle has been chosen, it is placed into the fluid sample and connected to the instrument using a screw assembly. The spindle ID is then entered into the memory of the instrument.
5) The desired rotational velocity is entered and the motor is switched on. At this point the spindle rotates at the desired velocity.
6) The digital display on the instrument provides for direct readout of temperature, shear rate, shear stress, strain gauge reading, and viscosity. Usually after about 1 minute the readings have stabilized. No calculations by the operator are required. When the readings have stabilized the pertinent information is recorded by the operator from the digital display.

Using Neutonian viscosity standards (Cannon Instrument Co., State College, Pa.) it was found that strain gauge readings between 20% and 100% viscosity results deviate from actual values by no more than 2%. Table 3 summarizes the results obtained in these viscosity determinations.

TABLE 3

| Average Carbon Number of Alkenyl Groups in the Alkenyl Succinic Anhydrides | Viscosity at 25° C., centipoise |
|---|---|
| 16.1 | 135.8 |
| 16.8 | 153.5 |
| 17.5 | 164.0 |
| 18.2 | 179.5 |
| 18.9 | 195.8 |
| 19.6 | 213.3 |

It is to be understood and appreciated that the foregoing Examples and experimental evaluations are presented for the purposes of illustration. They are not intended to constitute, and should not be construed as constituting, limitations on the scope of this invention.

Experimental work on related alkenyl succinic anhydrides indicates that there is a correlation between the sizing efficacy of such anhydrides and their viscosity, expressed as centistokes. In particular, it has been shown that alkenyl succinic anhydrides with viscosities in the range of 80 to 220 centistokes at 25° C. are highly effective internal sizing agents, i.e., when mixed with cellulosic pulp.

It will be appreciated that acylating agents corresponding to maleic anhydride can be used in preparing the alkenyl succinic anhydrides used in forming the alkenyl succinic anhydride mixtures of this invention. For example, maleic acid, the mono or dimethyl ester thereof, or the acid chlorides thereof can be used in lieu of, or in addition to, maleic anhydride. Because of its excellent reactivity, use of maleic anhydride itself is preferred. It will also be appreciated that essentially equivalent products can be formed by using acylating agents closely related to maleic anhydride such as citraconic anhydride, itaconic anhydride, dimethyl maleic anhydride, and their corresponding acids, lower alkyl esters, or acid halides.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions called for pursuant to this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A mixture of alkenyl succinic anhydrides in which the alkenyl groups have in the range of about 6 to about 40 carbon atoms, and in which at least 97 wt % of the alkenyl groups are bifurcated on the alpha carbon atom into two branches neither of which has less than two carbon atoms, said mixture being further characterized in that:

A) from about 20 to about 50% of the alkenyl succinic anhydrides that are bifurcated on the alpha carbon atom, have only one methyl or methylene group thereon, and the remainder of the alkenyl succinic anhydrides that are bifurcated on the alpha carbon atom have two straight chain branches emanating from the alpha carbon atom;

B) the alkenyl succinic anhydrides present in said mixture are composed of at least 3 alkenyl succinic anhydrides that differ from each other in the number of carbon atoms in the respective alkenyl groups, each of said at least 3 alkenyl succinic anhydrides being present in said mixture in an amount of at least 5 wt % based on the total weight of said mixture of alkenyl succinic anhydrides;

C) the alkenyl succinic anhydrides present in said mixture contain no more than about 50 wt % based on the total weight of said alkenyl succinic anhydrides, of any specific alkenyl succinic anhydride;

D) the alkenyl succinic anhydrides present in said mixture contain no more than about 50 wt % based on the total weight of said alkenyl succinic anhydrides, of any two or more alkenyl succinic anhydride isomers having the same number of carbon atoms in their alkenyl groups;

E) the alkenyl succinic anhydrides present in said mixture are proportioned such that the average number of carbon atoms in the alkenyl groups thereof is in the range of about 16 to about 22 carbon atoms per molecule; and F) said mixture of alkenyl succinic anhydrides has a viscosity at 25° C. in the range of about 80 to about 220 centistokes.

2. A mixture of alkenyl succinic anhydrides of claim 1 wherein the alkenyl succinic anhydrides present in said mixture are composed of at least 4 alkenyl succinic anhydrides that differ from each other in the number of carbon atoms in the respective alkenyl groups, each of said at least 4 alkenyl succinic anhydrides being present in said mixture in an amount of at least 5 wt % based on the total weight of said mixture of alkenyl succinic anhydrides; and wherein at least 98 wt % of the alkenyl succinic anhydrides in said mixture are bifurcated on the alpha carbon atom into two branches neither of which has less than two carbon atoms.

3. A mixture of alkenyl succinic anhydrides of claim 1 wherein the alkenyl succinic anhydrides present in said mixture contain no more than about 40 wt % based on the total weight of said alkenyl succinic anhydrides, of any specific alkenyl succinic anhydride; and wherein the alkenyl succinic anhydrides present in said mixture contain no more than about 40 wt % based on the total weight of said alkenyl succinic anhydrides, of any two or more alkenyl succinic anhydride isomers having the same number of carbon atoms in their alkenyl groups.

4. A mixture of alkenyl succinic anhydrides of claim 1 wherein the alkenyl succinic anhydrides present in said mixture are composed of at least 4 alkenyl succinic anhydrides that differ from each other in the number of carbon atoms in the respective alkenyl groups, each of said at least 4 alkenyl succinic anhydrides being present in said mixture in an amount of at least 5 wt % based on the total weight of said mixture of alkenyl succinic anhydrides; wherein at least 98 wt % of the alkenyl succinic anhydrides in said mixture are bifurcated on the alpha carbon atom into two branches neither of which has less than two carbon atoms; wherein the alkenyl succinic anhydrides present in said mixture contain no more than about 40 wt % based on the total weight of said alkenyl succinic anhydrides, of any specific alkenyl succinic anhydride; and wherein the alkenyl succinic anhydrides present in said mixture contain no more than about 40 wt % based on the total weight of said alkenyl succinic anhydrides, of any two or more alkenyl succinic anhydride isomers having the same number of carbon atoms in their alkenyl groups.

5. A mixture of alkenyl succinic anhydrides of any of claims 1–4 wherein at least about 95 wt % of the alkenyl succinic anhydrides present in said mixture have an even number of carbon atoms in their respective alkenyl groups.

6. A mixture of alkenyl succinic anhydrides of any of claims 1–4 wherein the components thereof have in the range of about 12 to about 30 carbon atoms in their respective alkenyl groups.

7. A mixture of alkenyl succinic anhydrides of any of claims 1–4 wherein the components thereof have in the range of about 14 to about 26 carbon atoms in their respective alkenyl groups.

8. A mixture of alkenyl succinic anhydrides of any of claims 1–4 wherein the mixture of alkenyl succinic anhydrides is in admixture with one or more saturated aliphatic hydrocarbons, the amount of said one or more saturated aliphatic hydrocarbons being up to about 5 wt % based on the total weight of said alkenyl succinic anhydrides and said one or more saturated aliphatic hydrocarbons.

9. A mixture of alkenyl succinic anhydrides of any of claims 1–4 wherein:

a) the alkenyl succinic anhydrides thereof have in the range of about 12 to about 30 carbon atoms in their respective alkenyl groups; and b) at least 98 wt % of the alkenyl succinic anhydrides present in said mixture have an odd or an even number of carbon atoms in their respective alkenyl groups.

10. A mixture of alkenyl succinic anhydrides of any of claims 1–4 wherein:

a) the alkenyl succinic anhydrides thereof have in the range of about 14 to about 26 carbon atoms in their respective alkenyl groups;

b) at least 98 wt % of the alkenyl succinic anhydrides present in said mixture have an even number of carbon atoms in their respective alkenyl groups; and c) the mixture of alkenyl succinic anhydrides contains, if any, no more than about 5 wt % of one or more saturated aliphatic hydrocarbons based on the total weight of said alkenyl succinic anhydrides and said one or more saturated aliphatic hydrocarbons.

11. A mixture of alkenyl succinic anhydrides of any of claims 1–4 wherein said mixture contains, if any, no more than a total of about 2 wt % of alkenyl succinic anhydrides in which the alkenyl groups contain 15, 16, 17, 18, or 19 carbon atoms.

12. A mixture of alkenyl succinic anhydrides of any of claims 1–4 wherein:

a) the alkenyl succinic anhydrides thereof have in the range of about 14 to about 26 carbon atoms in their respective alkenyl groups;

b) at least 98 wt % of the alkenyl succinic anhydrides present in said mixture have an odd or an even number of carbon atoms in their respective alkenyl groups;

c) the mixture of alkenyl succinic anhydrides contains, if any, no more than about 2 wt % of one or more saturated aliphatic hydrocarbons based on the total weight of said alkenyl succinic anhydrides and said one or more saturated aliphatic hydrocarbons; and d) said mixture contains, if any, no more than a total of about 2 wt % of alkenyl succinic anhydrides in which the alkenyl groups contain 15, 16, 17, 18, or 19 carbon atoms.

13. A mixture of alkenyl succinic anhydrides of any of claims 1–4 wherein at least about 70 wt % of the alkenyl groups have the olefinic double bond in the two or higher position.

14. A mixture of alkenyl succinic anhydrides of claim 1 wherein (1) from about 20 to about 80 wt % of the alkenyl groups of the alkenyl succinic anhydrides present in said mixture are $C_{14}$ alkenyl groups, and (2) from about 20 to about 80 wt % of the alkenyl groups of the alkenyl succinic anhydrides present in said mixture are in the range of $C_{20}$ to $C_{26}$ alkenyl groups, the total of the percentages of (1) and (2) being at least 90 wt %.

15. A mixture of alkenyl succinic anhydrides of claim 14 wherein the alkenyl groups that are in the range of $C_{20}$ to $C_{26}$ have even numbers of carbon atoms.

16. A mixture of alkyl succinic anhydrides in which the alkyl groups have in the range of about 6 to about 40 carbon atoms, and in which at least 97 wt % of the alkyl groups are bifurcated on the alpha carbon atom into two branches, neither of which has less than two carbon atoms, said mixture being further characterized in that:

A) from about 20 to about 50% of the alkyl succinic anhydrides that are bifurcated on the alpha carbon atom, have only one methyl group thereon, and the remainder of the alkyl succinic anhydrides that are bifurcated on the alpha carbon atom have two straight chain branches emanating from the alpha carbon atom;

B) the alkyl succinic anhydrides present in said mixture are composed of at least 3 alkyl succinic anhydrides that differ from each other in the number of carbon atoms in the respective alkyl groups, each of said at least 3 alkyl succinic anhydrides being present in said mixture in an amount of at least 5 wt % based on the total weight of said mixture of alkyl succinic anhydrides;

C) the alkyl succinic anhydrides present in said mixture contain no more than about 50 wt % based on the total weight of said alkyl succinic anhydrides, of any specific alkyl succinic anhydride;

D) the alkyl succinic anhydrides present in said mixture contain no more than about 50 wt % based on the total weight of said alkyl succinic anhydrides, of any two or more alkyl succinic anhydride isomers having the same number of carbon atoms in their alkyl groups;

E) the alkyl succinic anhydrides present in said mixture are proportioned such that the average number of carbon atoms in the alkyl groups thereof is in the range of about 16 to about 20 carbon atoms per molecule; and F) said mixture of alkyl succinic anhydrides has a viscosity at 25° C. in the range of about 80 to about 220 centistokes.

17. In a process of sizing a cellulose fiber in an aqueous paper-making slurry, the improvement which comprises introducing into said slurry as a sizing agent a mixture of alkenyl succinic anhydrides in which the alkenyl groups have in the range of about 6 to about 40 carbon atoms, and in which at least 97 wt % of the alkenyl groups are bifurcated on the alpha carbon atom into two branches neither of which has less than two carbon atoms, said mixture being further characterized in that:

A) from about 20 to about 50% of the alkenyl succinic anhydrides that are bifurcated on the alpha carbon atom, have only one methyl or methylene group thereon, and the remainder of the alkenyl succinic anhydrides that are bifurcated on the alpha carbon atom have two straight chain branches emanating from the alpha carbon atom;

B) the alkenyl succinic anhydrides present in said mixture are composed of at least 3 alkenyl succinic anhydrides that differ from each other in the number of carbon atoms in the respective alkenyl groups, each of said at least 3 alkenyl succinic anhydrides being present in said mixture in an amount of at least 5 wt % based on the total weight of said mixture of alkenyl succinic anhydrides;

C) the alkenyl succinic anhydrides present in said mixture contain no more than about 50 wt % based on the total weight of said alkenyl succinic anhydrides, of any specific alkenyl succinic anhydride;

D) the alkenyl succinic anhydrides present in said mixture contain no more than about 50 wt % based on the total weight of said alkenyl succinic anhydrides, of any two or more alkenyl succinic anhydride isomers having the same number of carbon atoms in their alkenyl groups;

E) the alkenyl succinic anhydrides present in said mixture are proportioned such that the average number of carbon atoms in the alkenyl groups thereof is in the range of about 16 to about 22 carbon atoms per molecule; and F) said mixture of alkenyl succinic anhydrides has a viscosity at 25° C. in the range of about 80 to about 220 centistokes.

18. The improvement according to claim 17 wherein said mixture of alkenyl succinic anhydrides is further characterized in that:

a) the alkenyl succinic anhydrides thereof have in the range of about 14 to about 26 carbon atoms in their respective alkenyl groups; and b) at least 98 wt % of the alkenyl succinic anhydrides present in said mixture have an even number of carbon atoms in their respective alkenyl groups.

19. The improvement according to claim 17 wherein said mixture of alkenyl succinic anhydrides is further characterized in that (i) from about 20 to about 80 wt % of the alkenyl groups of the alkenyl succinic anhydrides present in said mixture are $C_{14}$ alkenyl groups, (ii) from about 20 to about 80 wt % of the alkenyl groups of the alkenyl succinic anhydrides present in said mixture are in the range of $C_{20}$ to $C_{26}$ alkenyl groups, the total of the percentages of (i) and (ii) being at least 90 wt %, and (iii) at least about 70 wt % of the alkenyl groups have the olefinic double bond in the two or higher position.

* * * * *